(12) United States Patent
Anderson

(10) Patent No.: US 11,884,695 B2
(45) Date of Patent: Jan. 30, 2024

(54) HEAVY VITAMIN B12 DERIVATIVES

(71) Applicant: CHARLES STURT UNIVERSITY, Wagga Wagga (AU)

(72) Inventor: Peter Anderson, Orange (AU)

(73) Assignee: CHARLES STURT UNIVERSITY, Wagga Wagga (AU)

( * ) Notice: Subject to any disclaimer, the term of this patent is extended or adjusted under 35 U.S.C. 154(b) by 0 days.

(21) Appl. No.: 18/045,596

(22) Filed: Oct. 11, 2022

(65) Prior Publication Data
US 2023/0183287 A1 Jun. 15, 2023

Related U.S. Application Data

(63) Continuation of application No. 17/128,511, filed on Dec. 21, 2020, now Pat. No. 11,597,747, which is a continuation of application No. 15/546,628, filed as application No. PCT/AU2015/050027 on Jan. 28, 2015, now Pat. No. 10,899,789.

(51) Int. Cl.
*C07H 23/00* (2006.01)
*G01N 33/82* (2006.01)
*G01N 30/72* (2006.01)

(52) U.S. Cl.
CPC ......... *C07H 23/00* (2013.01); *G01N 30/7233* (2013.01); *G01N 33/82* (2013.01)

(58) Field of Classification Search
CPC ..... C07H 23/00; G01N 30/7233; G01N 33/82
See application file for complete search history.

(56) References Cited

U.S. PATENT DOCUMENTS

| 8,202,507 | B2 | 6/2012 | Anderson et al. |
| 2005/0222079 | A1 | 10/2005 | Goerne |
| 2006/0110322 | A1 | 5/2006 | Anderson et al. |
| 2021/0107935 | A1 | 4/2021 | Anderson |

OTHER PUBLICATIONS

Battersby et al., "Biosynthesis of Vitamin $B_{12}$: Evidence from Double-labelling Studies ($^{13}CD_3$) for Intact Incorporation of Seven Methyl Groups," Journal of the Chemical Society, Chemical Communications, 14, pp. 543-544 (1976).

Definition of Derivative by Merriam-Webster, 10 pages, found online at: http://beta.merriam-webster.com/dictionary/derivative (accessed Dec. 9, 2015).

Iida et al., "Metabolic pathways leading from amino acids to vitamin $B_{12}$ in *Propionibacterium shermanii*, and the sources of the seven methyl carbons," The FEES Journal, 274(19), pp. 5090-5095 (2007).

International Search Report and Written Opinion for International Patent Application No. PCT/AU2015/050027, dated Feb. 27, 2015 (9 pages).

Scott et al., "Biosynthesis of Corrinoids. Concerning the Origin of the Methyl Groups in Vitamin B12," Journal of the American Chemical Society, 94(23) pp. 8267-8269 (1972).

*Primary Examiner* — James W Rogers
(74) *Attorney, Agent, or Firm* — Mintz Levin Cohn Ferris Glovsky and Popeo, P.C.

(57) ABSTRACT

The invention discussed in this application relates to vitamin B12-based compounds that are useful as quantitative standards, particularly for the assessment of vitamin B12 deficiency.

20 Claims, 2 Drawing Sheets

HEAVY VITAMIN B12 DERIVATIVES

FIELD OF THE INVENTION

The present invention relates to vitamin B12-based compounds that are useful as quantitative standards. The present invention also relates to compositions including the compounds, and to methods of assessing patients for vitamin B12 deficiency using the compounds.

BACKGROUND OF THE INVENTION

Vitamin B12 (also known as cobalamin) is an essential vitamin that plays a key role in many physiological processes in the human body. However, it is not produced endogenously in fungi, plants, or animals, and can only be synthesised in nature by prokaryotes, such as bacteria [1]. Therefore, humans (and other animals) obtain their vitamin B12 from food or supplements. In addition, due to its chemical complexity, it is very difficult to synthesise vitamin B12 de novo and therefore, commercially, it is manufactured by microbial fermentation [2].

Vitamin B12 deficiency is a significant health concern—it can lead to megaloblastic anaemia and a range of neurological deficits (from peripheral neuropathy to depression, cognitive disturbances, and dementia). Evidence also suggests that vitamin B12 deficiency may contribute to the risk of vascular disease, cancer (particularly breast cancer), and neural tube defects (spina bifida, anencephaly). Vitamin B12 deficiency may also play a role in the rate of onset of clinical AIDS resulting from HIV infection.

The Schilling urinary excretion test [3] has been used since the 1950s to indirectly measure vitamin B12 absorption, and can be used when vitamin B12 insufficiency is identified and malabsorption is the suspected cause. The test involves ingestion of a physiological quantity of vitamin B12 labelled with radioactive (gamma-emitting) cobalt (such as $^{60}$Co or $^{57}$Co), followed by administration of a pharmacological parenteral flushing dose of unlabelled vitamin B12 to force urinary excretion of the radioactivity. Urine is collected over a 24-hour period, and the radioactivity in the urine is then measured. While the Schilling test has been the standard assessment for vitamin B12 absorption for many years, it does suffer from a number of disadvantages, including the use of radioactive isotopes (which exposes patients and medical personnel to small but quantifiable levels of gamma radiation, and results in the production of radioactive waste), and the long waiting period (24 hours for the first stage, which causes problems with patient compliance and delays treatment of the underlying condition).

US 2012/0264174 describes a method for preparing a labelled form of vitamin B12 for deficiency testing, as well as for determining the cause of the vitamin B12 deficiency. However, the labelled products produced using this method also have a number of drawbacks, including the use of $^{14}$C, which is a radioisotope (as discussed above, radioisotopes are a health and safety concern) and complex detection systems (specifically, accelerator mass spectrometry, or AMS).

AMS is a very specialised instrument that is not widely available, due to its size, complexity, initial expense and running costs. In addition, sample preparation for AMS is complicated by the fact that the sample needs to be pyrolysed (as it is the carbon isotopes in the resulting $CO_2$ that are detected and measured). The sample preparation method also means that AMS detects the ratio of all carbon isotopes in a sample, regardless of the source of the isotopes. For example, in the case of $^{13}$C, the natural abundance is around 1%, which consists of random incorporations of $^{13}$C in all carbon-containing compounds (including vitamin B12). AMS cannot tell the difference between these randomly incorporated $^{13}$C signals and small amounts of vitamin B12 labelled with $^{13}$C, essentially counting the labelled vitamin B12 and the background as one signal.

Therefore, the accuracy of the result of the analysis can be adversely affected, and is not solely dependent on the amount of labelled vitamin B12 administered to the patient for the analysis.

Accordingly, a simple, safe and accurate means for quantitative measurement of vitamin B12 in a variety of matrices (particularly biological matrices) is desirable.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention seeks to address one or more of the above mentioned problems, and/or to provide significant improvements in vitamin B12 detection and measurement and, in a first aspect, provides a heavy vitamin B12 derivative having a mass shift of at least +7 over unlabelled vitamin B12. In one embodiment, the heavy vitamin B12 derivative includes seven $^{13}$C atoms. In one embodiment, the seven $^{13}$C atoms are located in the dimethylbenzimidazole moiety of the vitamin.

In one embodiment, the heavy vitamin B12 derivative is a compound of formula (I), or a pharmaceutically acceptable salt, hydrate, solvate or prodrug thereof:

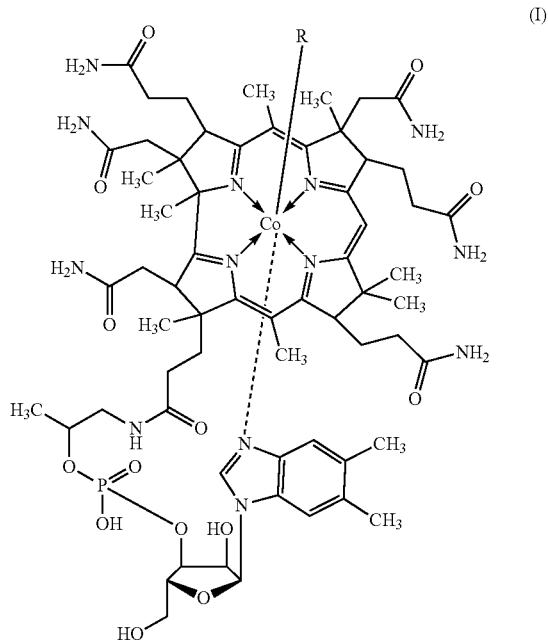

wherein
R is selected from 5'-deoxyadenosyl, OH, $H_2O$, $CH_3$ or CN, and seven of the carbon atoms of the dimethylbenzimidazole moiety are $^{13}$C atoms. In one embodiment, the $^{13}$C atoms are located only in the dimethylbenzimidazole moiety.

In one embodiment, the seven $^{13}$C atoms are located in the dimethylbenzimidazole moiety as follows:

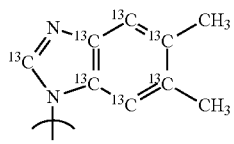

In one embodiment, the heavy vitamin B12 derivative further includes one or more deuterium (i.e. $^2$H) atoms (for example, two or three $^2$H atoms).

In a second aspect, the present invention relates to a process for preparing a heavy vitamin B12 derivative as described herein, the process including:
  providing $^{13}$C-labelled 5,6-dimethylbenzimidazole having seven $^{13}$C atoms,
  providing cobinamide dicyanide,
  contacting the $^{13}$C-labelled 5,6-dimethylbenzimidazole with the cobinamide dicyanide in the presence of a bacterium,
  thereby producing the heavy vitamin B12 derivative.

In one embodiment, the $^{13}$C-labelled 5,6-dimethylbenzimidazole has nine $^{13}$C atoms. In one embodiment, the $^{13}$C-labelled 5,6-dimethylbenzimidazole also includes one or more $^2$H atoms.

In one embodiment, the bacterium is *Salmonella enterica* (*S. enterica*). In one embodiment, the process is carried out under aerobic conditions. The process may be carried out in the presence of ethanolamine as the carbon source.

In one embodiment, the process includes the initial step of preparing the $^{13}$C-labelled 5,6-dimethylbenzimidazole having seven $^{13}$C atoms. In one embodiment, this includes:
  providing $^{13}$C-labelled formic acid,
  providing $^{13}$C-labelled dimethylphenylenediamine having six $^{13}$C atoms,
  contacting the $^{13}$C-labelled formic acid with the $^{13}$C-labelled dimethylphenylenediamine,
  thereby producing the $^{13}$C-labelled 5,6-dimethylbenzimidazole having seven $^{13}$C atoms.

In one embodiment, the process is carried out in the presence of heated (e.g. to boiling) hydrochloric acid as described by Phillips (1928) [4]. Purification of the $^{13}$C-labelled 5,6-dimethylbenzimidazole could be carried out, for example, as described in Carkeet et al (2006) [5].

In a third aspect, the present invention relates to a pharmaceutical composition including a heavy vitamin B12 derivative as described herein, and one or more pharmaceutically acceptable carrier substances, diluents or excipients.

In a fourth aspect, the present invention relates to a method of assessing a patient for vitamin B12 deficiency, the method including:
  administering to a patient an effective amount of a heavy vitamin B12 derivative as described herein,
  obtaining a biological fluid sample from the patient, and analysing the sample to determine the quantity of the heavy vitamin B12 derivative in the sample.

In a fifth aspect, the present invention relates to a method of assessing a patient for vitamin B12 deficiency, the method including:
  administering to a patient an effective amount of the pharmaceutical composition as described herein,
  obtaining a biological fluid sample from the patient, and analysing the sample to determine the quantity of the heavy vitamin B12 derivative in the sample.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
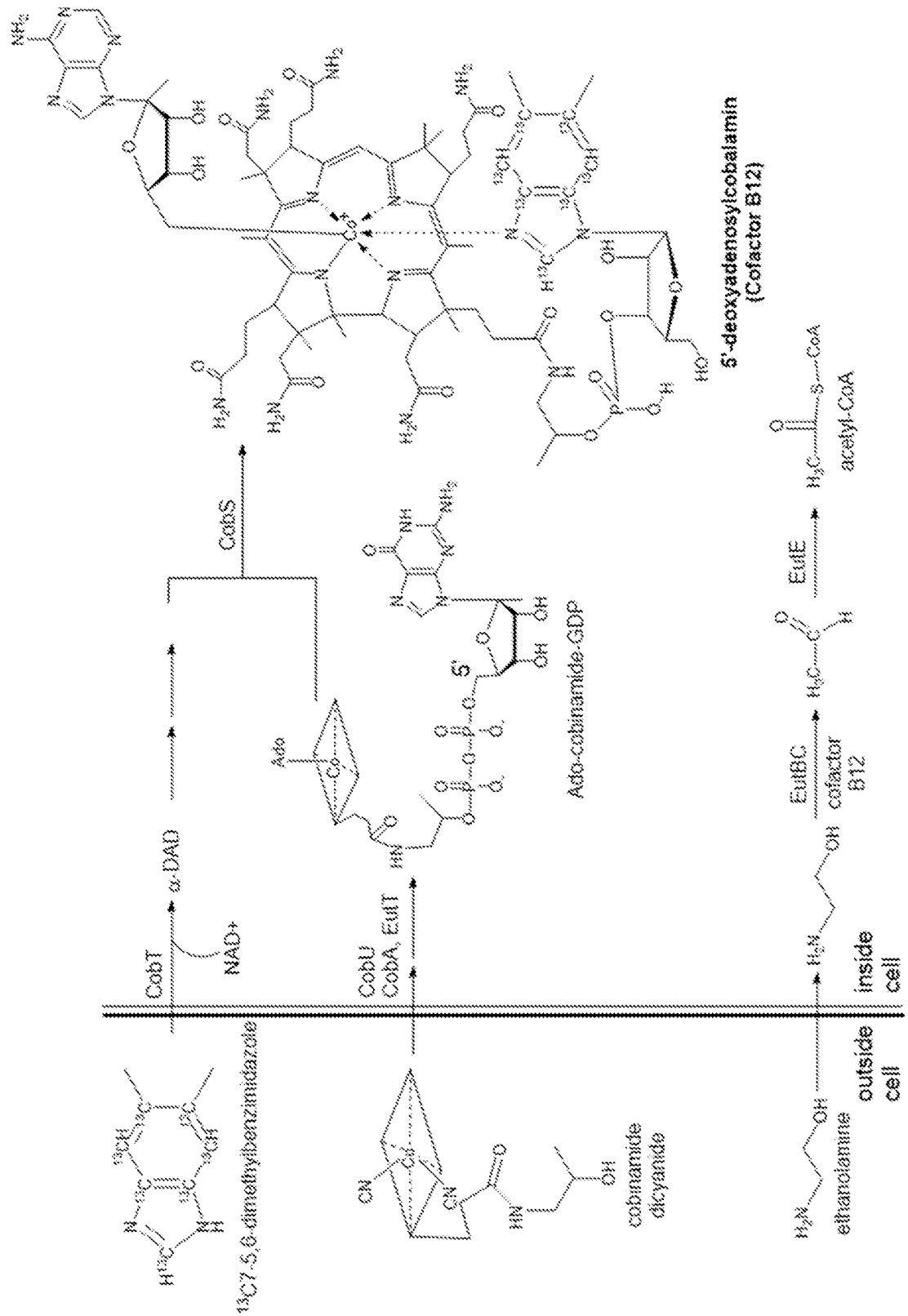
FIG. 1. Overview of the enzymatic synthesis of a purified heavy vitamin B12 derivative of the present invention ($^{13}$C$_7$-vitamin B12) mediated by cells of *Salmonella enterica*.
Figure 2:
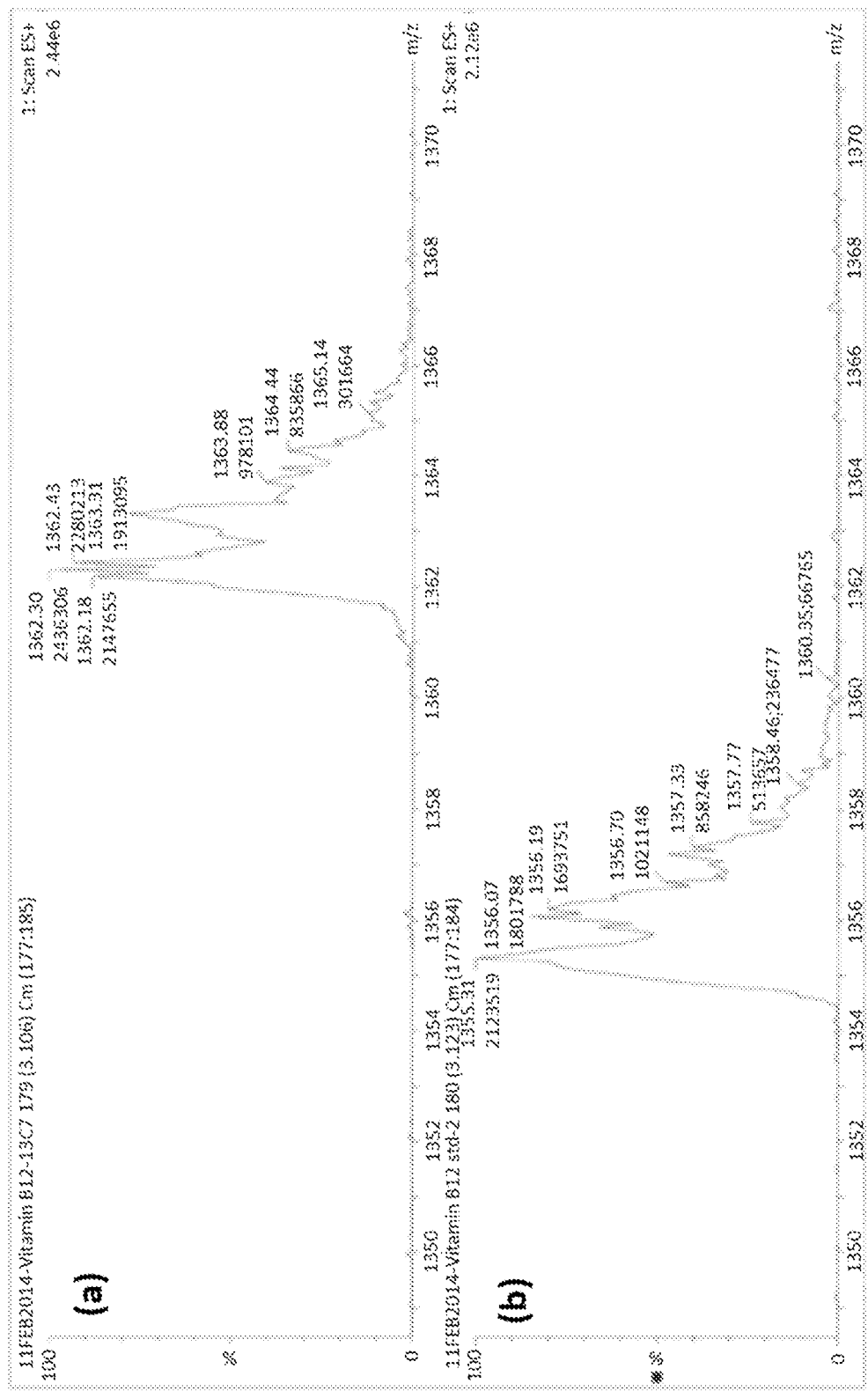
FIG. 2. Mass spectra of a purified heavy vitamin B12 derivative of the present invention ($^{13}$C$_7$-vitamin B12) of very high (>98%) specific activity, produced by the synthesis outlined in FIG. 1. (a) Mass spectrum of $^{13}$C$_7$-vitamin B12 produced through the S. enteric biosynthesis shows a primary ion m/z 1362, consistent with the expected +7 mass shift over unlabelled vitamin B12 due to incorporation of seven $^{13}$C atoms in the dimethylbenzimidazole moiety of the heavy vitamin B12 derivative. (b) Mass spectrum of unlabelled vitamin B12 shows the expected primary ion m/z of 1355 for comparative purposes. Note that both spectra in the figure have secondary m/z peaks due to incorporation of, for example, naturally occurring $^{13}$C.

The present inventors have found that a heavy vitamin B12 derivative having a mass shift of at least +7 over unlabelled vitamin B12 allows for better quantitation of vitamin B12, and allows quantitation in almost any biological matrix. This is, at least in part, due to the fact that the mass spectrometry signal obtained from the heavy vitamin B12 derivative of the present invention is outside the mass-measurement trace of standard (i.e. unlabelled) vitamin B12. This allows for quantification of both the labelled and unlabelled vitamin B12 in a sample, and also allows standard mass spectrometers to be used for the analysis. As mentioned above, current analysis methods use radioactive isotopes, are inconvenient to patients due to prolonged testing times, and/or require the use of expensive and complex equipment (e.g. AMS) to carry out the analyses.

In addition, because an exact amount of the heavy vitamin B12 derivative can be administered, and goes through identical processing to the unlabelled vitamin B12 in the sample to be analysed, if any losses of vitamin B12 occur during sample processing, the losses can be accounted for by the loss observed for the heavy vitamin B12 derivative. Therefore, quantitation of the amount of unlabelled vitamin B12 initially in the sample, prior to sample processing, can be calculated with greater accuracy than if the heavy vitamin B12 derivative was used at just the point of measurement. This is not possible using AMS-based techniques.

Further, unexpectedly, the heavy vitamin B12 derivative of the present invention can be prepared by the same bacteria as standard vitamin B12. This is not expected, as bacterial enzymes can be sensitive to isotopic changes, and large changes in mass (such as +7 mass units) to the substrate chosen for incorporation could not be expected to result in any incorporation of the substrate into the final vitamin B12 product.

It is well-known in the art that vitamin B12 actually consists of a class of chemically-related compounds (vitamers), all of which have vitamin activity. The two vitamins that participate in enzymatic reactions in human cells are methylcobalamin and deoxyadenosylcobalamin, which differ from each other in the identity of the p-axial ligand, as shown in formula (I) below:

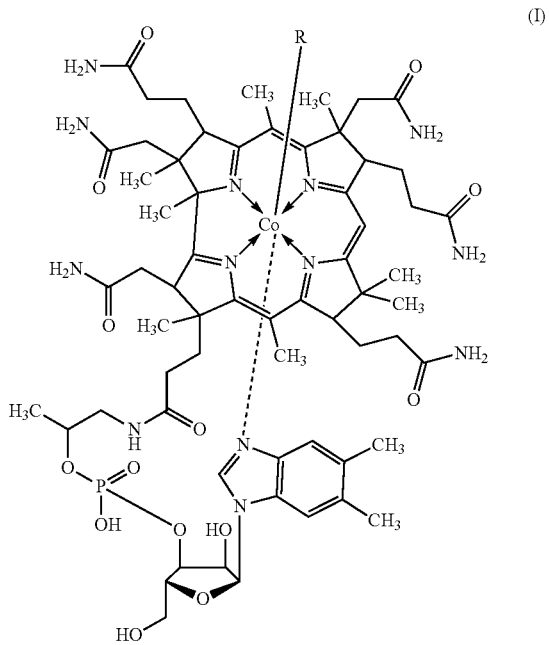

(I)

where R is $CH_3$, for methylcobalamin, and 5'-deoxyadenosyl for deoxyadenosylcobalamin. Other vitamers that are suitable for use in the present invention are hydroxycobalamin (where R is OH) and aquacobalamin (where R is $H_2O$).

There also exists a cyanocobalamin vitamer (where R is CN), which is not naturally occurring but is the form of the vitamin commonly used in dietary supplements, such as multivitamins, because it is a particularly stable form.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaieic, hydroiodic, phenylacetic, alkanoic (such as acetic, HOOC—$(CH_2)_n$—COOH where n is any integer from 0 to 6, i.e. 0, 1, 2, 3, 4, 5 or 6), and the like. Similarly, pharmaceutically acceptable cations include, but are not limited to, sodium, potassium, calcium, aluminum, lithium and ammonium. A person skilled in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent (such as ether, ethyl acetate, ethanol, isopropanol or acetonitrile), or in a mixture of the two.

It will be apparent that the compounds of the present invention may, but need not, be present as a hydrate or solvate. In addition, the various crystal forms and polymorphs are within the scope of the present invention, as are prodrugs of the compounds provided herein.

A "prodrug" is a compound that may not fully satisfy the structural requirements of the compounds provided herein, but is modified in vivo, following administration to a subject or patient, to produce a heavy vitamin B12 derivative as provided herein. For example, a prodrug may be an acylated derivative of a heavy vitamin B12 derivative. Prodrugs include compounds wherein hydroxyl or amine groups are bonded to any group that, when administered to a mammalian subject, cleaves to form a free hydroxyl or amine group, respectively. Examples of prodrugs include, but are not limited to, acetate, formate, phosphate and benzoate derivatives of amine functional groups within the heavy vitamin B12 derivative. Prodrugs of the may be prepared by modifying functional groups present in the compounds in such a way that the modifications are cleaved in vivo to generate the parent compounds.

As used herein, the term "heavy vitamin B12 derivative" refers to a vitamin B12 vitamer that includes, in its structure, one or more isotopes that result in the vitamer having a mass that is higher than that of standard vitamin B12. In accordance with the present invention, the heavy vitamin B12 derivative has a mass shift of at least +7 over unlabelled (or "standard") vitamin B12. This may be due to the presence of seven $^{13}C$ atoms. In one embodiment, the heavy vitamin B12 derivative has a mass shift of at least +9 over unlabelled (or "standard") vitamin B12. This may be due to seven $^{13}C$ atoms and two $^2H$ atoms, or due to nine $^{13}C$ atoms. In one embodiment, the $^{13}C$ atoms are located only in the dimethylbenzimidazole moiety. In one embodiment, the $^2H$ atoms are also located only in the dimethylbenzimidazole moiety.

A person skilled in the art will understand that standard vitamin B12 may include one or more additional isotopes as part of its structure—in particular, $^{13}C$ is a naturally occurring and stable (i.e. non-radioactive) isotope of carbon that is found in low abundance (about 1% compared to $^{12}C$ which has an abundance of around 99%). Therefore, the standard mass of vitamin B12, by natural incorporation of one or more $^{13}C$ isotopes, also varies and, when analysed by a mass spectrometer, will create a spectrum that includes, in addition to the "main" peak, multiple peaks for the various isotope-containing forms of the vitamin. These additional peaks have been termed a "shadow" or "trace", and make the analysis and quantification of known vitamin B12 derivatives difficult, as many of these derivatives have masses that fall within this "shadow". The present invention is based on the finding that, by using a heavy vitamin B12 derivative having a mass shift of at least +7 over unlabelled vitamin B12 (which has a mass ion of m/z 1355), the peak for the derivative appears well outside the shadow or trace, thereby allowing for simple and accurate quantification of both the standard vitamin B12 and the heavy vitamin B12 derivative.

In order to facilitate this increased resolution, it is preferred that the heavy vitamin B12 derivative exists predominantly as a single isotopic species, with a single mass, rather than multiple isotope mass variants. By "predominantly", it is meant that at least 90% of the heavy vitamin B12 derivative has a single mass. For example, at least 91%, at least 92%, at least 93%, at least 94%, at least 95%, at least 96%, at least 97%, at least 98% or at least 99% of the heavy vitamin B12 derivative has a single mass (e.g. +7 over unlabelled vitamin B12).

It is preferred that the mass shift from unlabelled vitamin B12 be as consistent as possible across the sample of labelled vitamin B12 as the natural abundance of $^{13}C$ in vitamin B12 means that at least a proportion of the unlabelled vitamin B12 will have a higher mass relative to the primary peak. Accordingly, in a preferred form, at least 90%, at least 91%, at least 92%, at least 93%, at least 94%, at least 94%, at least 95%, at least 96%, at least 97%, at least 98% or at least 99% of the heavy vitamin B12 has a single mass shift due to labelling with $^{13}C$ and/or $^2H$.

It is also preferred that the heavy vitamin B12 derivative does not contain significant amounts of vitamin B12 that is mass shifted by less than 7 atomic mass units over unlabelled vitamin B12. That is, the heavy vitamin B12 derivative has less than 10%, less than 9%, less than 8%, less than 7%, less than 6%, less than 5%, less than 4%, less than 3%, less than 2% or less than 1% of vitamin B12 that has a mass that is shifted by less than 7 atomic mass units over unlabelled vitamin B12.

In one embodiment, the heavy vitamin B12 derivative of the present invention has a primary mass ion of at least m/z 1362. If additional isotopes are incorporated into the structure of the heavy vitamin B12 derivative, then the mass will shift (as will the m/z of the primary mass ion). For example, if another $^{13}C$ atom is incorporated into the structure of the heavy vitamin B12 derivative, then the primary mass ion will have a m/z of 1363 (which corresponds to a mass shift of +8). The same change in mass will occur if a hydrogen atom is replaced with, for example, a deuterium atom ($^2H$). In one embodiment of the present invention, the heavy vitamin B12 derivative further includes one or more $^2H$ atoms (for example, two or three $^2H$ atoms). In one embodiment, the heavy vitamin B12 derivative further includes three $^2H$ atoms. If the heavy vitamin B12 derivative already includes seven $^{13}C$ atoms, then the total mass shift will be +10 over unlabelled vitamin B12. Therefore, in one embodiment, the heavy vitamin B12 derivative of the present invention has a mass shift of from +7 to +10 (i.e. +7, +8, +9, or +10) over unlabelled vitamin B12. This can be achieved by using only one type of isotope (e.g. only $^{13}C$) or a combination of isotopes (e.g. $^{13}C$ and $^2H$), as discussed.

The isotopes may be located anywhere in the vitamin B12 structure. In one embodiment, the isotopes (e.g. the seven $^{13}C$ atoms) are located in the dimethylbenzimidazole moiety of the vitamin. In one embodiment, the isotopes are located only in the dimethylbenzimidazole moiety of the vitamin. In one embodiment, additional isotopes (e.g. $^2H$ atoms) are also located in the dimethylbenzimidazole moiety of the vitamin.

The present invention also relates to a process for preparing a heavy vitamin B12 derivative of the present invention, the process including:
providing $^{13}C$-labelled 5,6-dimethylbenzimidazole having seven $^{13}C$ atoms,
providing cobinamide dicyanide,
contacting the $^{13}C$-labelled 5,6-dimethylbenzimidazole with the cobinamide dicyanide in the presence of a bacterium,
thereby producing the heavy vitamin B12 derivative.

In one embodiment, the $^{13}C$-labelled 5,6-dimethylbenzimidazole has eight $^{13}C$ atoms. In one embodiment, the $^{13}C$-labelled 5,6-dimethylbenzimidazole has nine $^{13}C$ atoms. In one embodiment, the $^{13}C$-labelled 5,6-dimethylbenzimidazole also includes one or more $^2H$ atoms. For example, the $^{13}C$-labelled 5,6-dimethylbenzimidazole may have seven $^{13}C$ atoms and two $^2H$ atoms.

Purified $^{13}C$-labelled 5,6-dimethylbenzimidazole (having seven, or more, $^{13}C$ atoms and optionally one or more $^2H$ atoms) can be obtained commercially from, for example, Isosciences LLC (PA, USA) cat #13422.

In one embodiment, the bacterium is *Salmonella enterica* (*S. enterica*). For example, *S. enterica* serovar *Typhimurium* (*S. typhimurium*) is a suitable species. A particularly suitable strain is PA09, which has a mutation that stops the bacterium from synthesising its own (i.e. unlabelled) vitamin B12, if during growth, it becomes anaerobic. In one embodiment, the process is carried out under aerobic conditions. The process may be carried out in the presence of ethanolamine as the carbon source.

An example of a process that is suitable in respect of the present invention is that described in Carkeet et al (2006) [5] (see FIG. 1). In summary, the bacterium is grown aerobically in a minimal growth medium with ethanolamine provided as the sole carbon source. Growth of the bacterium on ethanolamine is dependent on the presence of vitamin B12. Substrates $^{13}C_7$-5,6-dimethylbenzimidazole and cobinamide dicyanide are provided in the growth medium. Enzymes CobaT,U,S and EutT in the bacterial cells enable the synthesis to occur, the product is $^{13}C_7$-5'-deoxyadenosylcobalamin.

In one embodiment, the process includes the initial step of preparing the $^{13}C$-labelled 5,6-dimethylbenzimidazole having seven $^{13}C$ atoms. In one embodiment, this includes:
providing $^{13}C$-labelled formic acid
providing $^{13}C$-labelled dimethylphenylenediamine with six $^{13}C$ atoms
contacting the $^{13}C$-labelled formic acid with the $^{13}C$-labelled dimethylphenylenediamine,
thereby producing the $^{13}C$-labelled 5,6-dimethylbenzimidazole having seven $^{13}C$ atoms. $^{13}C$-labelled formic acid and $^{13}C$-labelled dimethylphenylenediamine having six $^{13}C$ atoms are available commercially, for example, from Cambridge Isotope Laboratories, Inc. (Tewksbury, MA, USA). $^{13}C$-labelled dimethylphenylenediamine having more than six $^{13}C$ atoms (e.g. eight $^{13}C$ atoms), and optionally one or more $^2H$ atoms, can also be obtained from commercial sources, such as Cambridge Isotope Laboratories, Inc. (Tewksbury, MA, USA).

In one embodiment, the process is carried out in the presence of heated (e.g. to boiling) hydrochloric acid. An example of a process that is suitable in respect of the present invention for the preparation of $^{13}C$-labelled 5,6-dimethylbenzimidazole is that described in Phillips (1928) [4].

The process described herein affords a simple and efficient means of providing the vitamin B12 derivative of the present invention. As discussed above, it was not expected by the inventors that the heavy vitamin B12 derivative of the present invention could be made in this manner as bacterial enzymes can be sensitive to isotopic changes, and large changes in mass (such as +7 mass units) to the substrate chosen for incorporation cannot be expected to result in incorporation of the substrate into the final vitamin B12 product.

The present invention also relates to a pharmaceutical composition including a heavy vitamin B12 derivative of the present invention, and one or more pharmaceutically acceptable carrier substances, diluents or excipients.

A "pharmaceutical carrier, diluent or excipient" includes, but is not limited to, any physiological buffered (i.e., about pH 7.0 to 7.4) medium including a suitable water soluble carrier, conventional solvents, dispersion media, fillers, solid carriers, coatings, antibacterial and antifungal agents, isotonic and absorption delaying agents. Suitable water soluble carriers include, but are not limited to water, saline, dextrose, corn oil, dimethylsulfoxide, and gelatin capsules. Other conventional additives include lactose, mannitol, corn starch, potato starch, binders such as crystalline cellulose, cellulose derivatives, acacia, gelatins, disintegrators such as sodium carboxymethyl-cellulose, and lubricants such as talc or magnesium stearate.

Pharmaceutical compositions may be formulated for any appropriate route of administration including, for example, topical (for example, transdermal or ocular), oral, buccal, nasal, vaginal, rectal or parenteral administration. In certain embodiments, compositions in a form suitable for oral use or parenteral use are preferred. Suitable oral forms include, for example, aqueous solutions, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Examples of components are described in Martindale—The Extra Pharmacopoeia (Pharmaceutical Press, London 1993).

The term "parenteral" as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Intravenous administration is preferred.

Suitable components of parenteral formulations, and methods of making such formulations, are detailed in various texts, including Martindale (as above) and "Remington's Pharmaceutical Sciences". Pharmaceutical compositions may include, for example, one or more of water, buffers (for example, neutral buffered saline, phosphate buffered saline, citrates and acetates), ethanol, oil, carbohydrates (for example, glucose, fructose, mannose, sucrose and mannitol), proteins, polypeptides or amino acids such as glycine, antioxidants (e.g. sodium bisulfite), tonicity adjusting agents (such as potassium and calcium chloride), chelating agents such as EDTA or glutathione, vitamins and/or preservatives. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials.

The present invention also relates to a method of assessing a patient for vitamin B12 deficiency, the method including:

administering to a patient an effective amount of a heavy vitamin B12 derivative according to the present invention or a pharmaceutical compositions according to the present invention, obtaining a biological fluid sample from the patient, and analysing the sample to determine the quantity of the heavy vitamin B12 derivative in the sample.

The term "effective amount" refers to an amount of the heavy vitamin B12 derivative of the present invention that results in a detectable amount of the derivative in the sample obtained from the patient. The dosage form and amount of the derivatives or pharmaceutical compositions of the present invention can be readily established by reference to known assays.

It will also be understood, that the specific dose level for any particular patient, and the length of time that the derivative will take to be present in the relevant biological fluid of the patient, will depend upon a variety of factors including the age, body weight, general health, sex, diet, time of administration, route of administration, and rate of absorption.

A person skilled in the art will know how much of the heavy vitamin B12 derivative to administer to a patient to achieve the optimal assessment capability without causing problems from a toxicity perspective. A suitable single dose of a heavy vitamin B12 derivative of the present invention is, for example, 1.5 micrograms administered orally in aqueous solution before a standard, small breakfast that is low in fat [6]. Therefore, in one embodiment, the heavy vitamin B12 derivative of the present invention is administered in an amount of about 1.5 micrograms. In one embodiment, the pharmaceutical composition of the present invention includes the heavy vitamin B12 derivative of the present invention in an amount of about 1.5 micrograms, and one or more pharmaceutically acceptable carrier substances, diluents or excipients.

The heavy vitamin B12 derivatives of the present invention find particular use in assisting clinicians to determine whether a patient has a vitamin B12 deficiency. The heavy vitamin B12 derivatives of the present invention can also be used to study the absorption of vitamin B12 in a subject, thereby assisting a clinician to determine whether a patient suffers from vitamin B12 malabsorption.

Patients may include but are not limited to primates, especially humans, domesticated companion animals such as dogs, cats, horses, and livestock such as cattle, pigs and sheep, with dosages as described herein.

The analysis of the biological sample obtained from the patient will generally be conducted using High Performance Liquid Chromatography (HPLC) with the output connected to a mass spectrometer. An example of an HPLC that would be suitable for the separation would be a Waters Alliance HPLC system (Waters, Rydalmere, NSW, Australia) connected to a reversed-phase C18:0 column. Mobile phases that would be suitable for the separation would be methanol and water, for example, as described by Carkeet et al (2006) [5]. An example of a mass spectrometer suitable for the analysis would be a single quadrupole mass spectrometer, such as the Advion Expression L (Advion, Inc. Ithaca, NY, USA) with an m/z range of up to 2,000.

Using this equipment for analysis of a heavy vitamin B12 derivative of the present invention, a 10 mL blood sample from a patient would be separated into three equal-volume subsamples: subsample 1, subsample 2 and subsample 3. To subsample 1, $^{13}C_7$-cyanocobalamin would be added in an exact amount, such as 10 ng. To subsample 2, $^{13}C_7$-methylcobalamin would be added in an exact amount, such as 10 ng. To subsample 3, $^{13}C_7$-adenosylcobalamin would be added in an exact amount, such as 10 ng. The red blood cells would be separated from the serum by, for example, centrifugation at 2500×g for 20 minutes. Serum would then be applied to, for example, a solid-phase extraction cartridge such as a C18:0 column (Waters) after preparation following the manufacturer's instructions. The column would be washed with three bed volumes of sterile water, and eluted with one column volume of 100% methanol. The subsamples are then dried under vacuum at 45° C., dissolved in 50 microlitres of water and each sample individually applied to the HPLC/MS.

It will be understood that the invention disclosed and defined in this specification extends to all alternative combinations of two or more of the individual features mentioned or evident from the text or drawings. All of these different combinations constitute various alternative aspects of the invention.

EXAMPLES

Synthesis

Biosynthesis of $^{13}C_7$-cyanocobalamin ($^{13}C_7$-B12)

For details regarding the bacterial growth media used in these Examples, see further below.

*Salmonella enterica* strain PA09 (Charles Sturt University, Orange, NSW, Australia) is streaked for single colonies onto LB plates and incubated aerobically at 37° C. for 15 hours. A single colony of PA09 is then inoculated, using aseptic technique, into 10 mL of sterile LB broth, which is grown aerobically until cells are at stationary phase, typically for 8-12 hours at 37° C. with shaking at 200 RPM. One mL of this LB broth is then inoculated into 100 mL sterile NCE broth supplemented with 1% sterile glycerol, and is then grown aerobically for 24 hours with shaking at 200 RPM. The 100 mL NCE/Glycerol broth is then used to inoculate 1% vol/vol 4 litres of sterile NCE growth medium, supplemented with final concentrations of: sterile ethanolamine 40 mM as sole carbon source, sterile 0.5 micromolar dicyanocobinamide and sterile 2 micromolar $^{13}C_7$-dimethylbenzimidazole. The 4 L of NCE culture is then grown aerobically, for instance in 1 L Schott Bottles in a shaking incubator at 37° C. for 48 hours, until cells have grown to an optical density of at least 1.0 and typically 1.50 as measured at 600 nm on a spectrophotometer. The bacterial cells are harvested by centrifugation at 20,000×g for 20 minutes and the supernatant is removed and discarded (or unincorporated substrates may also be recovered if desired).

Extraction of $^{13}C_7$-B12 from Bacterial Cells

Cell pellets are resuspended in an equal volume of NCE medium and then 9 further volumes of ethanol are added to the cells. Under a fume hood, between 2-5 mg of sodium cyanide is added to the mixture. The mixture is capped, then heated for 60-120 minutes at 45° C. with shaking. The resultant mixture is centrifuged at 20,000×g for 20 minutes, the pink supernatant containing the $^{13}C_7$-B12 is removed and dried under vacuum at 55° C., and resuspended in 2 mL of Milli-Q (deionised) water. The pink-coloured mixture is applied to a C18:0 solid phase extraction cartridge (Waters) pre-prepared in accordance with the manufacturer's instructions. The $^{13}C_7$-B12 and other related compounds bind to the C18:0 solid phase cartridge. The column is then washed with 10 volumes of Milli-Q water to remove polar contaminants. Partially purified $^{13}C_7$-B12 is eluted from the column with two bed volumes of ethanol, then dried under vacuum at 60° C.

HPLC Purification of $^{13}C_7$-B12

Purification of the $^{13}C_7$-B12 is achieved by reversed-phase HPLC on an Eclipse XBD C18 column 4.6 mm×150 mm, 3.5 micro with the following run conditions: Mobile Phase A: $H_2O$ with 0.1% formic acid Mobile Phase B: Acetonitrile. Pump 5-35% B over 10 minutes, 35-95B over 10 minutes. UV followed at 361 nm. Flow rate 1 mL/minute.

The peak eluting at 6.162 minutes with a width of 0.24 minutes is $^{13}C_7$-B12. It is collected at around 96% purity. The process is repeated on this setup, using an autoinjector, until all the $^{13}C_7$-B12 has been purified.

Bacterial Growth Media For Synthesis of $^{13}C_7$-B12

LB Plates (1 Litre)
Add the following to 800 mL $H_2O$
10 g Bacto-tryptone
5 g Yeast extract
10 g NaCl
15 g bacterial grade Agar
Adjust to pH 7.5 with NaOH, if necessary
Adjust volume to 1 L with $H_2O$ (milliQ)
Autoclave 121° C./15 minutes wet cycle
LB Broth (1 litre)
Add the following to 800 mL $H_2O$
10 g Bacto-tryptone
5 g Yeast extract
10 g NaCl
Adjust to pH 7.5 with NaOH, if necessary
Adjust volume to 1 L with $H_2O$ (milliQ)
Autoclave 121° C./15 minutes wet cycle
NCE-Ethanolamine Growth Medium (500 mL Volume)
10 mL of 50× NCE Salts Solution
50 mL of ethanolamine stock solution
MilliQ water up to 500 mL Autoclave on gentle cycle—121° C., for 30 mins
50× NCE salts (1 Litre Volume)
Heat 330 mL $dH_2O$ on stirring block (do not boil)
Dissolve chemicals one at the time in the order listed below, allowing each to dissolve completely before the next addition
197 g $KH_2PO_4$
323 g $K_2HPO_4 \cdot 3H_2O$ (246.6 g for anhydrous)
175 g $NaNH_4HPO_4 \cdot 4H_2O$
Bring to 1000 mL total volume with $dH_2O$
Autoclave 121° C. on the liquid cycle
Store at 4° C. to limit loss of ammonium ions as ammonia
1 M $MgSO_4$ (50× Stock, 100 mL Volume)
24.65 g $MgSO_4$ (246.5 g/mol)
100 mL $dH_2O$
Filter sterilize or autoclave. Store at room temperature.
Ethanolamine (10× stock, 500 mL Volume)
16 g Ethanolamine HCL (Sigma)
500 mL $H_2O$
Autoclave at 121° C. on the liquid cycle.

REFERENCES

1. Roth, J. R., Lawrence, J. G. and Bobik, T. A. *Cobalamin (coenzyme B12): synthesis and biological significance.* Annu Rev Microbiol, 1996. 50: p. 137-81.
2. Battersby, A. R., *How nature builds the pigments of life: the conquest of vitamin B12.* Science, 1994. 264(5165): p. 1551-7.
3. Schilling, R., *The effect of gastric juice on the urinary excretion of radioactivity after the oral administration of radioactive Vitamin $B_{12}$.* J Lab Clin Med, 1953. 42(6): p. 860-866.
4. Phillips, M. A., *The Formation of 2-Substituted Benzimi-nazoles.* J Chem Soc, 1928: p. 2393-2399.
5. Carkeet, C., et al., *Human vitamin B12 absorption measurement by accelerator mass spectrometry using specifically labeled $^{14}C$-cobalamin.* Proc Natl Acad Sci USA, 2006. 103(15): p. 5694-5699.
6. Lamar, C., et al., *Experiences with the Schilling Test as a Diagnostic Tool.* The American Journal of Clinical Nutrition, 1965. 16(5): p. 402-411.

The invention claimed is:

1. A heavy vitamin B12 having a mass shift of at least +8 over unlabelled vitamin B12, wherein the heavy vitamin B12 comprises eight or nine $^{13}C$ atoms and the eight or nine $^{13}C$ atoms are located in the dimethylbenzimidazole moiety of the vitamin.

2. The heavy vitamin B12 of claim 1, comprising eight $^{13}C$ atoms.

3. The heavy vitamin B12 of claim 1, comprising nine $^{13}C$ atoms.

4. The heavy vitamin B12 of claim 1, wherein the heavy vitamin B12 has a mass shift of from +8 to +11 over unlabelled vitamin B12.

5. The heavy vitamin B12 of claim 4, wherein the heavy vitamin B12 has a mass shift of +8 over unlabelled vitamin B12.

6. The heavy vitamin B12 of claim 4, wherein the heavy vitamin B12 has a mass shift of +9 over unlabelled vitamin B12.

7. The heavy vitamin B12 of claim 4, wherein the heavy vitamin B12 has a mass shift of +10 over unlabelled vitamin B12.

8. The heavy vitamin B12 of claim 4, wherein the heavy vitamin B12 has a mass shift of +11 over unlabelled vitamin B12.

9. The heavy vitamin B12 of claim 1, wherein the heavy vitamin B12 is a compound of formula (I), or a pharmaceutically acceptable salt, hydrate, solvate or prodrug thereof:

(I)

wherein
R is 5'-deoxyadenosyl, OH, $H_2O$, $CH_3$, or CN.

10. The heavy vitamin B12 of claim 9, wherein the pharmaceutically acceptable salt is selected from the group consisting of hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaieic, hydroiodic, phenylacetic, alkanoic, sodium, potassium, calcium, aluminum, lithium, and ammonium salts.

11. The heavy vitamin B12 of claim 1, wherein the heavy vitamin B12 further comprises one or more $^2H$ atoms.

12. The heavy vitamin B12 of claim 11, wherein the heavy vitamin B12 further comprises two $^2H$ atoms.

13. The heavy vitamin B12 of claim 11, wherein the one or more $^2H$ atoms are also located in the dimethylbenzimidazole moiety of the vitamin.

14. The heavy vitamin B12 of claim 1, wherein at least 90% of the molecules in the heavy vitamin B12 have a single mass shift.

15. The heavy vitamin B12 of claim 14, wherein at least 95% of the molecules in the heavy vitamin B12 have a single mass shift.

16. A pharmaceutical composition comprising the heavy vitamin B12 of claim 1, and one or more pharmaceutically acceptable carrier substances, diluents or excipients.

17. A method of assessing a patient for vitamin B12 deficiency, the method comprising:
administering to a patient an effective amount of the heavy vitamin B12 of claim 1, or a pharmaceutical composition thereof,
obtaining a biological fluid sample from the patient, and analysing the sample to determine the quantity of the heavy vitamin B12 in the sample.

18. The method of claim 17, wherein the biological fluid sample is a blood sample.

19. The method of claim 18, wherein the red blood cells are separated from the serum.

20. The method of claim 17, wherein the heavy vitamin B12 is administered parenterally or orally.

* * * * *